(12) United States Patent
Smith et al.

(10) Patent No.: US 8,211,072 B2
(45) Date of Patent: Jul. 3, 2012

(54) OSTOMY BAG

(75) Inventors: Rory James Maxwell Smith, Leatherhead (GB); Paul Bird, Copthorne (GB); Owen May, Maidstone (GB)

(73) Assignee: Welland Medical Limited (GB)

(*) Notice: Subject to any disclaimer, the term of this patent is extended or adjusted under 35 U.S.C. 154(b) by 336 days.

(21) Appl. No.: 12/549,914

(22) Filed: Aug. 28, 2009

(65) Prior Publication Data

US 2011/0054425 A1    Mar. 3, 2011

(51) Int. Cl.
*A61F 5/448* (2006.01)
*B32B 27/08* (2006.01)

(52) U.S. Cl. .................. 604/342; 604/344; 156/254

(58) Field of Classification Search .......... 604/332–345; 156/252–254
See application file for complete search history.

(56) References Cited

U.S. PATENT DOCUMENTS

| | | | | |
|---|---|---|---|---|
| 3,612,053 A * | 10/1971 | Pratt | ............................. | 604/338 |
| 3,780,739 A * | 12/1973 | Frank | ............................. | 604/335 |
| 3,802,436 A * | 4/1974 | Brondberg | .................... | 604/344 |
| 3,908,658 A * | 9/1975 | Marsan | .......................... | 604/336 |
| 3,948,256 A * | 4/1976 | Schneider | .................... | 604/344 |
| 4,085,752 A * | 4/1978 | Canale | ........................... | 604/370 |
| 4,213,458 A * | 7/1980 | Nolan et al. | ................... | 604/344 |
| 4,356,819 A * | 11/1982 | Potaczek | ......................... | 602/56 |
| 4,376,799 A * | 3/1983 | Tusim | .......................... | 428/213 |
| 4,403,991 A * | 9/1983 | Hill | ............................... | 604/337 |
| 4,445,898 A * | 5/1984 | Jensen | ........................... | 604/337 |
| 4,477,325 A * | 10/1984 | Osburn | .......................... | 264/488 |
| 4,573,984 A * | 3/1986 | Benzies | ......................... | 604/339 |
| 4,701,169 A * | 10/1987 | Steer | ............................... | 604/344 |
| 4,816,027 A | 3/1989 | Gilchrist | | |
| 4,826,495 A * | 5/1989 | Petersen | ........................ | 604/333 |
| 4,894,058 A * | 1/1990 | Jensen | ........................... | 604/332 |
| 4,946,720 A * | 8/1990 | Oishi et al. | ................... | 428/35.4 |
| 5,423,783 A * | 6/1995 | Battles et al. | ................. | 604/344 |

(Continued)

FOREIGN PATENT DOCUMENTS

EP    0259184 A1    3/1988

(Continued)

OTHER PUBLICATIONS

UK Search Report for UK Patent Application No. 0915054.1 (GB2473044) mailed Dec. 21, 2009.

(Continued)

*Primary Examiner* — Melanie Hand
*Assistant Examiner* — Paula Craig
(74) *Attorney, Agent, or Firm* — Heslin Rothenberg Farley & Mesiti P.C.

(57) ABSTRACT

The invention provides an ostomy bag assembly including an outer bag and an inner bag secured to one side of a flange. The inner bag is removable to facilitate disposal. The flange has a polymeric backing film and a layer of bioadhesive for securing the ostomy bag assembly to the body of a patient. The flange includes an orifice to enable bodily waste to be received by the inner bag. The outer bag is detachably bonded to a first attachment zone on the flange and the inner bag is secured to a second attachment zone on the flange. The outer bag is mounted to the flange by an annular bonding element is formed from a multilayer polymeric material comprising first and second ethylene vinyl acetate layers and a polymeric support layer interposed there between. A method of fabricating ostomy bags is also provided.

8 Claims, 2 Drawing Sheets

U.S. PATENT DOCUMENTS

| | | | |
|---|---|---|---|
| 5,429,626 A * | 7/1995 | Fenton | 604/339 |
| 5,545,154 A * | 8/1996 | Oberholtzer | 604/336 |
| 5,567,489 A * | 10/1996 | Allen et al. | 428/34.1 |
| 5,591,144 A | 1/1997 | Smith et al. | |
| 5,690,622 A | 11/1997 | Smith et al. | |
| 5,709,673 A * | 1/1998 | Keyes | 604/332 |
| 5,722,965 A * | 3/1998 | Kuczynski | 604/344 |
| 5,785,695 A | 7/1998 | Sato et al. | |
| 5,800,415 A * | 9/1998 | Olsen | 604/336 |
| 5,865,819 A | 2/1999 | Cisko | |
| 5,895,694 A * | 4/1999 | Zavadsky et al. | 428/36.7 |
| 5,938,647 A | 8/1999 | Smith | |
| 5,968,024 A * | 10/1999 | Freeman | 604/334 |
| 6,626,878 B1 * | 9/2003 | Leisner et al. | 604/339 |
| 6,966,901 B2 * | 11/2005 | Leisner et al. | 604/337 |
| 7,416,543 B2 * | 8/2008 | Brown et al. | 604/332 |
| 2004/0059306 A1 | 3/2004 | Tsal et al. | |
| 2004/0228992 A1 * | 11/2004 | Giori | 428/35.7 |
| 2005/0113770 A1 * | 5/2005 | Pedersen et al. | 604/332 |
| 2010/0121290 A1 * | 5/2010 | Rasmussen et al. | 604/333 |
| 2011/0125115 A1 * | 5/2011 | Anders et al. | 604/344 |
| 2011/0238024 A1 | 9/2011 | Smith et al. | |

FOREIGN PATENT DOCUMENTS

| | | |
|---|---|---|
| EP | 0320895 A1 | 6/1989 |
| GB | 2273052 A | 8/1994 |
| GB | 2290713 A | 10/1996 |
| GB | 2311469 A | 1/1997 |
| GB | 2329838 A | 7/1999 |
| GB | 2422312 A | 7/2006 |
| GB | 2434316 A | 7/2007 |
| NL | 2005450 | 12/2010 |
| WO | 9601089 | 1/1996 |
| WO | 0110363 A1 | 2/2001 |
| WO | 2004082452 A2 | 9/2004 |
| WO | 2005082271 A2 | 9/2005 |
| WO | 2006077438 A1 | 7/2006 |
| WO | 2010122314 A1 | 10/2010 |

OTHER PUBLICATIONS

EPO Search Report for European Patent Application No. 10251523.6 (EP2289471) mailed Dec. 23, 2010.

* cited by examiner

OSTOMY BAG

FIELD OF THE INVENTION

This invention relates to drainage bag assemblies, such as ostomy bags, for receiving bodily waste, and more particularly to an ostomy bag containing a removable inner liner.

BACKGROUND OF THE INVENTION

Ostomy bags for receiving bodily waste from colostomy and ileostomy patients are well known. One of the problems faced by users of ostomy bags, particularly colostomy bags, is how to dispose of the contents of the bag.

Many known forms of ostomy bag are made from materials that are not biodegradable and are not easily flushed down a W.C. (that is, a toilet) because of, for example, the buoyancy and relative bulk of the bags. With non-flushable bags, it has been common practice to cut an edge of the bag and then deposit the contents of the bag in the W.C. for flushing away, leaving the soiled bag for separate disposal, e.g. by incineration or by wrapping and placing in a waste bin.

One solution to this problem has been to provide ostomy bags made from materials that are capable of being flushed down a W.C. and examples of such bags are disclosed in WO 94/12128; EP 0259184; US 2004/0059306; EP 0320895; U.S. Pat. No. 5,989,235; GB 2083762; EP 388924; GB 2227668; GB 2193925; and WO 2007/085803.

In many cases, the flushable ostomy bag comprises an inner bag which is formed from a material that disintegrates or dissolves in water or is otherwise disposable and a protective outer bag formed from a material that is resistant to water. The outer bag can be constructed so as to be reusable several times, means being provided for opening the outer bag to permit removal and replacement of the inner bag or liner. The outer and inner bags may both be attached, directly or indirectly, to an adhesive flange which comprises a layer of a bio-compatible adhesive such as a hydrocolloid adhesive to secure the ostomy bag to the body of the patient about the stomal opening.

US 2004/0059306 in particular describes several forms of construction of two piece ostomy bags in which the inner bag or liner is replaceable and a re-fastenable opening is provided in the outer bag to give access to the inner bag so that it can be replaced.

U.S. Pat. No. 5,785,695 (Alcare) discloses ostomy appliances comprising inner and outer bags that are releasably attached to an adhesive flange by means of mechanical couplings comprising coupling rings having annular grooves that engage corresponding annular rims on the adhesive flange to form snap-fit connections.

US 2003/0153883 (Hansen) discloses ostomy appliances comprising an adhesive flange to which is secured a first mechanical coupling ring for the attachment of an outer bag. An inner bag or liner can also be secured to the first mechanical coupling ring by means of a second mechanical coupling ring which encircles the mouth of the inner bag and which forms a snap-fit connection against the radially inner surface of the first mechanical coupling ring.

A problem with ostomy appliances employing coupling rings to connect the inner and outer bags to an adhesive flange is that the coupling rings almost invariably make the appliance stiffer and less flexible and hence less comfortable to wear. In addition, where the coupling rings for the inner and outer bags are placed relatively close together, this can make separation and replacement of the bags difficult, particularly for people with impaired or reduced manual dexterity. A further problem with using coupling rings is that they will need to be removed prior to disposal of an inner bag down a WC. Not only does this add an additional potentially awkward step to the removal and disposal process but it may also result in the user's hands coming into contact with fecal waste at the mouth of the bag.

As an alternative to using mechanical couplings, adhesive bonding has been used to secure the inner and outer bags to the adhesive flange. Examples of ostomy bags making use of adhesive bonding can be found in U.S. Pat. No. 5,865,819 (Hollister) and WO 2004/082452 (Coloplast). U.S. Pat. No. 5,865,819 discloses an arrangement in which the inner and outer bags each have their own separate adhesive flange for direct connection to the body of the patient.

WO 2004/082452 discloses ostomy bags comprising an adhesive flange for attachment to the body of a patient, and inner and outer bags. The inner and outer bags are each provided with adhesive rings for attachment to the adhesive flange. In the preferred ostomy bag constructions disclosed in WO 2004/082452, the outer diameter of the adhesive ring of the inner bag is larger than the inner diameter of the adhesive ring of the outer bag and hence there is overlap between the two adhesive rings.

WO 2007/085803 discloses an ostomy bag assembly comprising inner and outer bags secured to an adhesive flange.

SUMMARY OF THE INVENTION

The present invention provides an ostomy bag assembly comprising outer and inner bags secured to one side of a flange; wherein:

the flange comprises a polymeric backing film and a layer of bioadhesive for securing the ostomy bag assembly to the body of a patient;

the flange has means defining an orifice to enable bodily waste to be received by the inner bag;

the outer bag is detachably bonded to a first attachment zone on the polymeric backing film of the flange by means of an annular bonding element which is interposed between the outer bag and the first attachment zone;

the inner bag is secured to a second attachment zone on the polymeric backing film of the flange;

the first attachment zone surrounds the second attachment zone and is non-overlapping therewith;

the second attachment zone surrounds the means defining the orifice;

the annular bonding element is formed from a multilayer polymeric material comprising first and second ethylene vinyl acetate layers and a polymeric support layer interposed therebetween;

the first ethylene vinyl acetate layer has a coating of an ethylene vinyl acetate copolymer adhesive thereon; and the first ethylene vinyl acetate layer is bonded to the polymeric backing film of the flange by means of the coating of ethylene vinyl acetate copolymer adhesive, and the second ethylene vinyl acetate layer is welded to the outer bag.

Particular and preferred embodiments of the invention are as set out in the claims appended hereto or in the paragraphs below.

The polymeric backing film comprises a layer of polyurethane film. Preferably, the polymeric backing film consists of a single layer of polyurethane film. The annular bonding element is formed from a multilayer polymeric material comprising first and second ethylene vinyl acetate layers and a polymeric support layer interposed there between. The multilayer polymeric material is typically a coextruded film.

The polymeric support layer is selected from polymers that are compatible with ethylene vinyl acetate (EVA) (for example, can form a strong bond to the EVA during the coextrusion process) and which are typically of greater tensile strength than EVA. For example, the polymeric support layer may be a polyamide or an ethylene/methacrylic acid co-polymer or an ionomeric form thereof. A particular example of a material suitable for use as the polymeric support layer is Surlyn® (partially neutralized ethylene acid copolymer).

The total thickness of the multilayer polymeric material can be, for example, from 120 micrometers (µm) to 180 µm, more typically from 140 µm to 160 µm, for example approximately 150 µm.

A particular example of the multilayer polymeric material is the PerfecSeal® coated PerfecFlex® medical forming film (partially neutralized ethylene acid copolymer laminated with EVA) available from Perfecseal Limited of Londonderry, Northern Ireland, UK, or its equivalent.

The coating of ethylene vinyl acetate copolymer adhesive on one side of the annular bonding element is bonded to the polyurethane film. Preferably, the bond to the polyurethane film is achieved by means of heat sealing by the application of heat and light pressure using an appropriately shaped heat sealing tool. By way of example, a temperature of about 120 degrees C. to about 160 degrees C. may typically be applied for a period of about 2 to about 5 seconds.

When the annular bonding element is formed from a multilayer polymeric material comprising first and second ethylene vinyl acetate layers and a polymeric support layer interposed therebetween, one of the EVA layers is coated with the ethylene vinyl acetate copolymer adhesive and the other EVA layer is uncoated. The uncoated layer is bonded to the outer bag, for example by means of welding, for example, RF welding.

Preferably, the outer bag is formed from a multilayer polymeric film comprising a layer of ethylene vinyl acetate and a layer of polyvinyl dichloride or polyvinyl chloride, the ethylene vinyl acetate layer being bonded to the uncoated EVA layer of the annular bonding element. More preferably the outer bag is formed from a multilayer polymeric film comprising two layers of ethylene vinyl acetate with a layer of polyvinyl dichloride sandwiched there between.

The bond between the annular bonding element and the first attachment zone on the polymeric backing film of the flange is peelable, for example, the annular bonding element and the attached outer bag can be peeled away from the flange using only manual force. Once the outer bag and annular bonding element have been peeled away from the polymeric backing film, it is typically not possible to reattach them to the polymeric backing film by finger pressure alone as the ethylene vinyl acetate copolymer adhesive does not retain any adhesive capability at ambient temperature after the two surfaces to which it is bonded have been peeled apart.

In order to assist the annular bonding element and attached outer bag to be peeled away from the polymeric backing film of the flange, the annular bonding element may be provided with one or more tabs. The (or each) tab may be formed from a polyethylene foam material.

The material from which the outer bag is formed typically is substantially impermeable to flatus gases and in particular the noxious components of flatus gases. Preferably therefore, in order to prevent the build up of flatus gases inside the ostomy bag assembly, the outer bag is provided with a flatus gas vent opening covered by a filter, which permits gases to exit the bag but filters out malodorous and noxious gases. Such filters are well known and need not be described here.

In the drainage bags of the invention, the attachment zones for the inner and outer bags do not overlap, and, in this respect, the bags differ from the ostomy bags disclosed in US 2004/0059306 and WO 2004/082452, where the attachment zones for the inner and outer bags are shown as overlapping. In the bags of the present invention, the first and second attachment zones may be contiguous or they may be spaced apart. Preferably, they are spaced apart.

The inner bag is secured by means of adhesive to the second attachment zone on the flange. The adhesive may be, for example a pressure sensitive adhesive or a non-pressure-sensitive adhesive. The adhesive can be located on the second attachment zone, or on a ring surrounding the mouth of the inner bag, or on both. In one embodiment, the inner bag is provided with a ring of adhesive surrounding the mouth of the bag.

The inner bag may be formed from a non-disposable waterproof material of a type described above for the outer bag, but preferably the inner bag is formed from a material that is biodegradable or disposable, such as polyvinyl alcohol. For example, the inner bag can be formed from a polymer, such as polyvinyl alcohol, of a type or grade that is slowly soluble in cold water but is more soluble in hot water. Examples of types of polyvinyl alcohol suitable for use in the fabrication of inner bags or liners are described in our earlier application WO94/12128.

In one embodiment, the inner bag comprises an inner layer formed from a hot water soluble grade of polyvinyl alcohol and an outer layer formed from a non-woven tissue comprising cold water-soluble polyvinyl alcohol fibres and water-insoluble polymer fibers (for example, cellulosic or modified cellulosic fibres such as rayon fibers). The inner and outer layers are preferably secured together at their peripheries.

In another aspect, the invention provides a process for manufacturing an ostomy bag assembly comprising outer and inner bags secured to one side of a flange; wherein:

the flange comprises a polymeric backing film, a layer of bioadhesive for securing the ostomy bag assembly to the body of a patient, and a removable protective layer covering the layer of bioadhesive;

the flange has means defining an orifice to enable bodily waste to be received by the inner bag;

the outer bag is detachably bonded to a first attachment zone on the polymeric backing film of the flange;

the inner bag is secured to a second attachment zone on the polymeric backing film of the flange by means of a pressure sensitive adhesive;

the first attachment zone surrounds the second attachment zone and is non-overlapping therewith;

the second attachment zone surrounds the means defining the orifice;

the first attachment zone is defined by an annular bonding element which is formed from a multilayer polymeric material comprising first and second ethylene vinyl acetate layers and a polymeric support layer interposed therebetween;

the first ethylene vinyl acetate layer has a coating of an ethylene vinyl acetate copolymer adhesive thereon;

and wherein the first ethylene vinyl acetate layer is bonded to the polymeric backing film of the flange by means of the coating of ethylene vinyl acetate copolymer adhesive, and the second ethylene vinyl acetate layer is bonded to the outer bag;

which process comprises, or comprises the steps of:

(a) forming the flange by punching a datum hole in a wafer comprising the polymeric backing film, layer of bioadhesive and removable protective layer;

(b) die cutting the annular bonding element from a web of the multilayer polymeric material;

(c) placing the annular bonding element on to the flange so that the annular bonding element is disposed concentrically with respect to the datum hole;
(d) heat sealing the annular bonding element to the flange;
(e) bringing into contact with the flange a web of a material from which a panel of the outer bag is to be formed and welding the said web to an inner edge of the annular bonding element;
(f) placing the inner bag on the flange and applying pressure to thereto to bond the pressure sensitive adhesive to the second attachment zone;
(g) bringing into contact with the said web a further web of a material from which another panel of the outer bag is to be formed and outline welding the webs together so that they form the outer bag and enclose the inner bag; and thereafter
(i) cutting the webs to release the ostomy bag assembly.

Prior to die cutting the annular bonding element in step (b), one or more tabs (for example, formed form a polyethylene foam material) may be attached to the web of the multilayer polymeric material. The annular bonding element with tab attached may then be cut from the web.

After the heat sealing the annular bonding element to the flange in step (d), the flange is preferably turned over and left to cool with the annular bonding element facing downwards, thereby preventing curling. The cooled annular bonding element and flange assembly may then be placed in a magazine in preparation for the welding step (e).

The process may optionally include a further process step of enlarging the datum hole to accommodate a defined size of stoma in a patient. The outer bag may comprise outer and inner pairs of panels welded together around their peripheries, the inner pair of panels serving to provide a waterproof and odour-proof containment for the inner bag and the outer pair of panels serving as a comfort layer. The comfort layer may typically be formed from a non-woven fibrous material such as a non-woven polyethylene fabric formed from polyethylene fibers.

Further aspects and embodiments of the invention will be apparent from the following brief description of the drawings and the detailed description below.

BRIEF DESCRIPTION OF THE DRAWINGS

In FIG. 1, internal features of the assembly are shown by means of dotted lines.

DETAILED DESCRIPTION OF THE INVENTION

Figure 1:
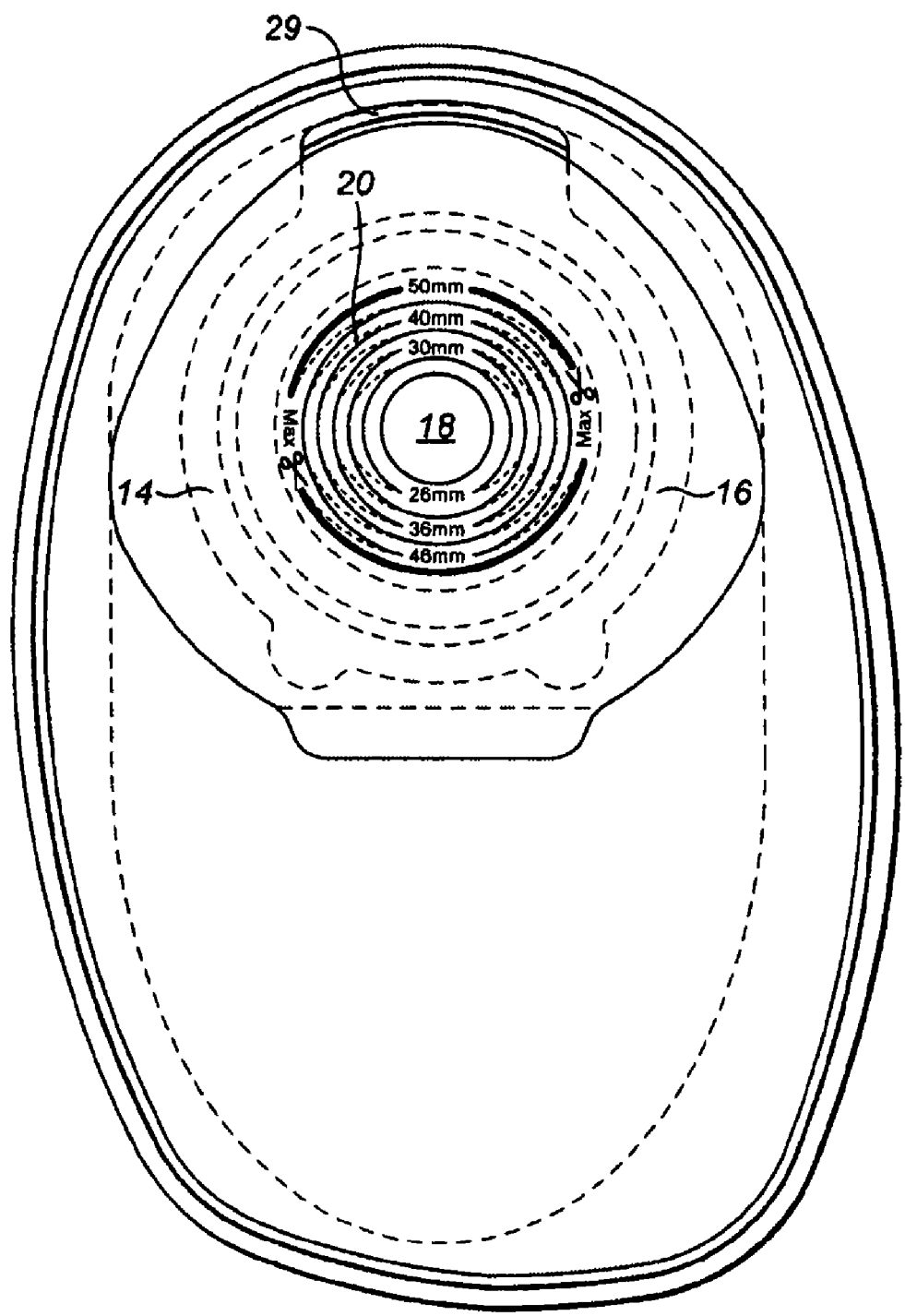
FIG. 1 is a plan view of an ostomy bag assembly according to one embodiment of the invention.

The invention will now be described in more detail, but not limited, by reference to the specific embodiments illustrated in the drawings.

Figure 2:
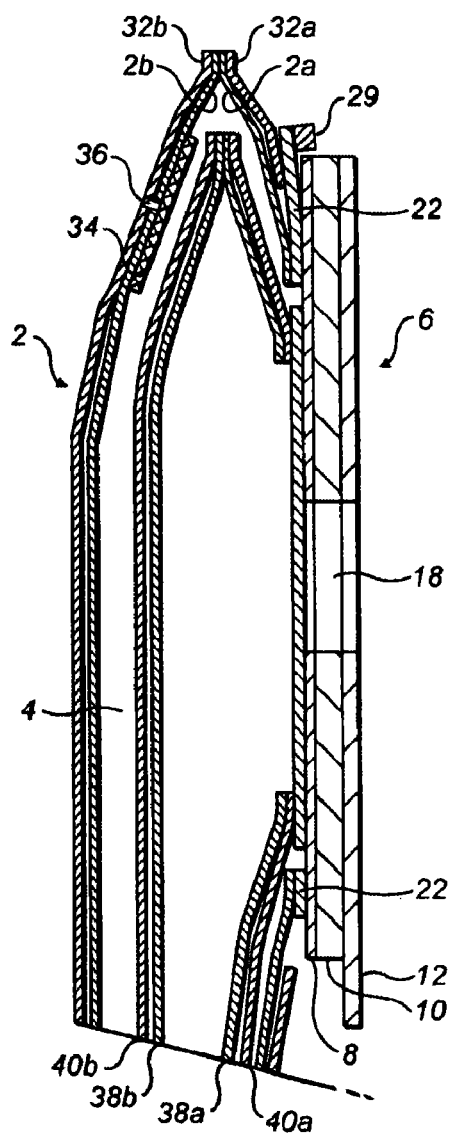
FIG. 2 is a side sectional elevation through the upper part of the ostomy bag assembly of FIG. 1.
Figure 3:
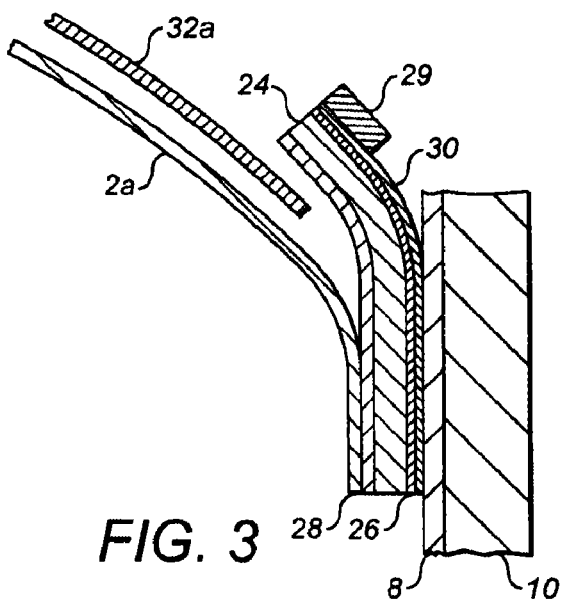
FIG. 3 is an enlarged view of the region A in FIG. 2.

Referring now to the drawings, FIGS. 1 to 3 show an ostomy bag assembly according to a first embodiment of the invention. The ostomy bag assembly of FIGS. 1 to 3 comprises an outer bag 2 and an inner bag 4 attached to an adhesive flange 6.

The adhesive flange 6 comprises a polymeric backing film 8 which, in this embodiment is formed from polyurethane and has a thickness of approximately 30 μm. Supported on the backing film 8 is a layer 10, approximately 0.6 millimeters (mm) to 0.9 mm thick, of a hydrocolloid. The hydrocolloid adhesive, which may be of conventional type, serves to secure the ostomy bag to the body of a patient. A siliconized paper release layer 12 covers the hydrocolloid adhesive layer and protects the adhesive layer against damage and/or drying out prior to use of the bag.

On the side of the flange opposite to the hydrocolloid adhesive is an area of the backing film 8 which constitutes a first attachment zone and which is designated in FIG. 1 by the dotted line 14. An area of the backing film which constitutes a second attachment zone is designated in FIG. 1 by the dotted line 16.

The flange has means defining an orifice to enable bodily waste to be received by the inner bag. As shown in FIG. 1, the flange has a central hole 18, the primary purpose of which is to serve as a datum hole for alignment of the various component parts of the ostomy bag assembly during manufacture. Arranged around the hole 18 is an array of concentric cutting lines 20 which are marked on the surface of the silicone release layer 12. By way of example, cutting lines are provided for apertures having diameters of 25 mm, 30 mm, 35 mm, 35 mm, 40 mm, 45 mm and 50 mm but cutting lines of different diameters could be used instead. In use, the patient or medical professional will select an aperture size to suit the stoma of a particular patient and will then cut along the appropriate cutting line to form the required aperture.

As an alternative, the datum hole may be widened by an additional cutting step during manufacture to give a range of standard size openings. In many cases, a patient may be able to fit the ostomy bag with a standard sized opening to the stoma without further cutting the adhesive flange. However, in cases where the patient's stoma does not conform to one of the range of standard openings, the patient can select the nearest undersized standard opening and then trim it to fit around his or her stoma.

It will be appreciated from the foregoing that the "means defining an orifice to enable bodily waste to be received by the inner bag" can take the form of an orifice or hole per se or can take the form of markings, score lines, perforations or skip cuts that indicate where a section of the flange may be removed to form or enlarge an opening.

The outer bag 2 is detachably bonded to the first attachment zone 14 on the polymeric backing film 8 of the flange by means of an annular bonding element 22 which is interposed between the first attachment zone 14 and the outer bag.

The annular bonding element is shown in more detail in the enlarged view provided in FIG. 3. As can be seen from FIG. 3, the annular bonding element comprises a co-extruded multilayer polymeric material which, in the particular embodiment illustrated, consists of a central layer 24 Surlyn® (partially neutralized ethylene acid copolymer) sandwiched between two layers 26 and 28 of ethylene vinylacetate (EVA). One of the EVA layers has a layer of an EVA copolymer adhesive emulsion 30 coated onto it: the other EVA layer is uncoated. The EVA adhesive-coated co-extruded multilayer polymeric material can be, for example, PerfecSeal coated PerfecFlex® medical forming film (partially neutralized ethylene acid copolymer laminated with EVA) available from Perfecseal Limited of Londonderry, UK.

The outer bag 2 is firmly bonded to the uncoated EVA layer 28 by welding, for example, by radio-frequency (RF) welding. This ensures a secure bond between annular bonding element and outer bag which cannot be disrupted without tearing the fabric of the outer bag.

The EVA adhesive-coated layer 26, 30 of the annular bonding element 22 is bonded to the first attachment zone 14 by aligning the bonding element 22 in the area of the attachment zone and applying heat with an annular heat sealing tool at a temperature of about 120 degrees C. to about 160 degrees C. for a period of about 2 to about 5 seconds. The EVA adhesive functions as a hot melt adhesive that forms a bond which, whilst easily strong enough to withstand any forces to which it is subjected during use, can be peeled apart using reasonable manual force to separate the outer bag from the adhesive flange. Once peeled away, the outer bag and annular bonding element cannot be reattached to the attachment zone without heat sealing since the EVA adhesive does not have any significant adhesive capability at room temperature and pressure.

In order to assist the annular bonding element 22 to be peeled away from the adhesive flange, a tab 29 is provided. The tab 29 is formed from 0.6 mm thick polyethylene foam coated on one side with a pressure sensitive adhesive to secure it to the annular bonding element 22.

Disposed within the outer bag 2, is an inner bag or liner 4. The inner bag or liner 12 is provided with a ring of pressure sensitive adhesive (not shown), which bonds to polyurethane backing film 8 flange at the second attachment zone 16.

The outer bag 2 in this embodiment can be formed from materials well known for the construction of ostomy bags. Thus, for example, it can be formed from a tough, flexible, transparent, waterproof material such as polyvinyl dichloride (PVDC), ethylene vinyl acetate (EVA), related materials and combinations thereof in known fashion, one particular material being the EVA/PVDC/EVA film available from Sealed Air of Saddle Brook, N.J., US under the trade name Cryovac MF514, or its equivalent.

In the embodiment shown, the outer bag is formed from a pair of sheets 2a and 2b of the flexible waterproof material, one sheet 2a being cut so as to form an opening, the edge of which is welded to the annular bonding element, and the other sheet 2b having the same outer periphery, but no opening. The two sheets are secured together around their respective peripheries by welding, (for example, by RF welding) or by means of adhesive. Attached to the sheets 2a and 2b by welding around their respective peripheries are panels 32a, 32b formed from a fibrous non-woven material, such as, a non-woven polyethylene fabric. The panels 32a and 32b serve as a comfort layer, providing a warmer and less harsh feeling against the skin of the patient.

The polymeric materials from which the sheets 2a and 2b are formed act as a barrier to gases, and in particular flatus gases. Therefore, in order to prevent ballooning of the ostomy bag through the build up of flatus gases inside the bag, the outer bag is provided with a small opening 36 covered by a flatus filter 34 which is welded to both the sheet 2b and the panel 32b.

The inner bag 4 is formed from two pairs of sheets 38a, 38b and 40a, 40b of polymeric material, welded together along their peripheries. The inner pair of sheets 38a and 38b is formed from a mechanically tough warm water soluble grade of polyvinyl alcohol film, for example, a "Solublon EF" (Trade Mark) film available from Aichello, Japan, or its equivalent. The outer pair of sheets 40a, 40b is formed from a fibrous non-woven tissue formed from cold water soluble polyvinyl alcohol fibres and rayon fibres, which disintegrates in water.

In use, fecal material from a stomal opening passes through the opening 18 (enlarged where necessary) in the flange and into the interior of the inner bag or liner 4. When the inner bag or liner 4 is full, the outer bag 2 and the attached annular bonding layer 22 are peeled away from the flange. The flange and inner bag may then be disposed of by flushing down a W.C. (that is, a toilet) and the outer bag disposed of through normal domestic waste channels. A new assembly of inner and outer bag and adhesive flange may then be applied to the patient.

Because the inner bag is formed from materials that are soluble or disintegrable in water, and the hydrocolloid adhesive of the flange is also soluble or erodible in water, the sub-assembly of flange and inner bag rapidly disintegrates during flushing leaving as a residue only the thin polyurethane backing film 8 and rayon fibers from the sheets 40a and 40b.

The ostomy bag assembly of the invention can be manufactured by a largely automated production process requiring relatively little manual intervention.

Wafers or blanks which will become the adhesive flange 6 are die cut from sheets of a trilaminar material consisting of the polyurethane backing film 8, hydrocolloid adhesive 10 and siliconised paper 12. The wafers can be prepared off site or manufactured in situ. The wafers are loaded into a magazine and are transferred on a rotating carousel to a cutting station where a datum hole 18 is die cut in the centre of the wafer. The hole 18 serves as the datum point for the alignment of the various components of the ostomy bag assembly later in the manufacturing process.

In a separate operation, polyethylene foam tabs are applied to a web of a coextruded multilayer film consisting of Surlyn® (partially neutralized ethylene acid copolymer) sandwiched between two layers of ethylene vinylacetate (EVA), one of which is coated with a layer of an EVA copolymer adhesive emulsion. The tabs are bonded to the web by means of a pressure sensitive adhesive. Rings of the multilayer film with a tab attached are then die cut from the web to form the annular bonding elements 22.

The annular bonding elements 22 are then automatically conveyed to another work station where they are placed over an adhesive flange wafer so that the annular bonding element is concentric with the datum hole 18 in the wafer. Heat and pressure are then applied to the annular bonding element to form a heat seal between the annular bonding element and the polyurethane backing film of the bonding element.

Once the heat seal has been created, the sub-assembly of adhesive flange and annular bonding element is removed, turned over and placed on a tray to cool with the annular bonding element facing down so as to prevent curling.

After cooling, the adhesive flange-annular bonding element sub-assemblies are loaded into a magazine with the annular bonding element facing up and transferred to a separate machine for creating the ostomy bags.

In a first step in the creation of the ostomy bags, a first web of a non-woven fabric (from which comfort panel 32a is made) is die cut to form a series of circular holes. A second web, which is formed from an EVA/PVDC/EVA film (which will become panel 2a) is then die cut with a series of holes of a smaller diameter than the holes in the first web. The first and second webs are then secured together by means of peripheral tack welds.

Adhesive flange-annular bonding element sub-assemblies are then transferred from their magazine to a welding station where they are successively welded to the second web so that each sub-assembly surrounds one of the holes in the web.

The first and second webs carrying the adhesive flange-annular bonding element sub assemblies pass through a further processing station where pre-formed inner bags, each having an opening surrounded by a ring of pressure sensitive adhesive, are affixed to the annular bonding elements.

At a separate filter welding station, a third web of material, from which the panel 2b will be formed, and a fourth web of material, from which the panel 32b will be formed, are brought together and a filter 34 is welded to the surface of the third web. The welding operation is carried out for a period of time sufficient to ensure that the fourth web is also welded to the third web in the region of the filter. The region over the filter where the third and fourth webs are welded together is then perforated to form an exit hole for flatus gases passing through the filter.

Once the filter has been affixed, the first, second, third and fourth webs are passed through another welding station where the four webs are outline welded together (the outline of the weld defining the shape of the ostomy bag). The webs are then cut around the outer edge of the outline to release the completed ostomy bag assembly from the webs. The completed ostomy bag assemblies may then be inspected and packed.

During the assembly of the ostomy bag, a further and optional cutting step may be employed in which the datum hole is enlarged to a size suitable for fitting about a stomal opening. During this step, differently sized cutters may be used for different batches thereby enabling the creation of a range of ostomy bags with different sizes of opening.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. An ostomy bag assembly comprising outer and inner bags secured to one side of a flange; wherein:
    the flange comprises a polymeric backing film and a layer of bioadhesive for securing the ostomy bag assembly to the body of a patient;
    the flange has means defining an orifice to enable bodily waste to be received by the inner bag;
    the outer bag is detachably bonded to a first attachment zone on the polymeric backing film of the flange by means of an annular bonding element which is interposed between the outer bag and the first attachment zone;
    the inner bag is secured to a second attachment zone on the polymeric backing film of the flange;
    the first attachment zone surrounds the second attachment zone and is non-overlapping therewith;
    the second attachment zone surrounds the means defining the orifice;
    the annular bonding element is formed from a multilayer polymeric material comprising first and second ethylene vinyl acetate layers and a polymeric support layer interposed therebetween;
    the first ethylene vinyl acetate layer has a coating of an ethylene vinyl acetate copolymer adhesive thereon; and
    the first ethylene vinyl acetate layer is bonded to the polymeric backing film of the flange by means of the coating of ethylene vinyl acetate copolymer adhesive, and the second ethylene vinyl acetate layer is welded to the outer bag.

2. An ostomy bag assembly according to claim 1, wherein the polymeric backing film comprises a layer of polyurethane film, and the said coating of ethylene vinyl acetate copolymer adhesive is peelably bonded to the polyurethane film.

3. An ostomy bag assembly according to claim 2, wherein the polymeric backing film comprises a single layer of polyurethane film.

4. An ostomy bag assembly according to claim 2, wherein the polymeric backing film consists of a single layer of polyurethane film.

5. An ostomy bag assembly according to claim 1, wherein the outer bag is formed from a multilayer polymeric film comprising a layer of ethylene vinyl acetate and a layer of polyvinyl dichloride or polyvinyl chloride; and wherein the ethylene vinyl acetate layer of the outer bag is bonded to the first attachment zone.

6. An ostomy bag assembly according to claim 5, wherein the multilayer polymeric film comprises two layers of ethylene vinyl acetate with a layer of polyvinyl dichloride sandwiched therebetween.

7. An ostomy bag assembly according to claim 1, wherein the first and second attachment zones are spaced apart.

8. An ostomy bag assembly according to claim 1, wherein the inner bag is formed from a biodegradable material or a material that dissolves or disintegrates upon flushing down a toilet.

* * * * *